US006727217B1

(12) United States Patent
Nieendick et al.

(10) Patent No.: US 6,727,217 B1
(45) Date of Patent: Apr. 27, 2004

(54) COLD PRODUCTION METHOD FOR PEARLY LUSTRE SURFACTANT PREPARATIONS

(75) Inventors: Claus Nieendick, Krefeld (DE); Karl Heinz Schmid, Mettmann (DE); Anke Eggers, Duesseldorf (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 10/009,289

(22) PCT Filed: Apr. 28, 2000

(86) PCT No.: PCT/EP00/03853

§ 371 (c)(1),
(2), (4) Date: Nov. 6, 2001

(87) PCT Pub. No.: WO00/68355

PCT Pub. Date: Nov. 16, 2000

(30) Foreign Application Priority Data

May 7, 1999 (DE) ........................................ 199 21 187

(51) Int. Cl.[7] .................................................. A61K 7/50

(52) U.S. Cl. ....................... 510/416; 510/119; 510/130; 510/123; 510/421; 424/70.19; 424/70.21

(58) Field of Search ................................ 510/119, 130, 510/123, 421, 476; 424/70.19, 70.21, 70.31; 516/77, 928

(56) References Cited

U.S. PATENT DOCUMENTS

| | | | |
|---|---|---|---|
| 4,777,038 | A | 10/1988 | Scheuffgen |
| 5,403,508 | A | 4/1995 | Reng et al. |
| 5,711,899 | A | 1/1998 | Kawa et al. |
| 6,121,331 | A | 9/2000 | Ansmann et al. |

FOREIGN PATENT DOCUMENTS

| | | | |
|---|---|---|---|
| DE | 1 165 574 | | 3/1964 |
| DE | 20 24 051 | C3 | 12/1971 |
| DE | 36 17 306 | A1 | 11/1986 |
| DE | 38 43 572 | A1 | 6/1990 |
| DE | 41 03 551 | A1 | 8/1992 |
| EP | 0 181 773 | B1 | 5/1986 |
| EP | 0 205 922 | A2 | 12/1986 |
| EP | 0 285 389 | B1 | 10/1988 |
| EP | 0 581 193 | A2 | 2/1994 |
| EP | 0 569 843 | B1 | 11/1995 |
| EP | 0 684 302 | A1 | 11/1995 |
| GB | 962919 | | 7/1964 |
| GB | 1 333 475 | | 10/1973 |
| WO | 92/13512 | A1 | 8/1994 |
| WO | 97/47719 | A | 12/1997 |

OTHER PUBLICATIONS

Ansmann, et al., "Perlglanz in modernen, tensidhaltigen Formulierungen", Parfümerie und Kosmetik, vol. 75, (1994), pp. 578–580.

Falbe, "Surfactants in Consumer Products", Springer Verlag, Berlin, (1987), pp. 54–124.

Falbe, "Katalysatoren, Tenside und Mineralöladditive" (Catalysts, Surfactants and Mineral Oil Additives), Thieme Verlag, Stuttgart, (1987), pp. 123–217.

*Primary Examiner*—Necholus Ogden
(74) *Attorney, Agent, or Firm*—John E. Drach

(57) ABSTRACT

Pearlescent surfactant compositions are prepared at a temperature of from about 10° C. to about 45° C. by providing an aqueous surfactant solution and then contacting the aqueous surfactant solution with a composition comprised of a pearlizing wax and a polyol ester.

9 Claims, No Drawings

COLD PRODUCTION METHOD FOR PEARLY LUSTRE SURFACTANT PREPARATIONS

BACKGROUND OF THE INVENTION

This invention concerns generally with pearlescent preparations and especially with cosmetics and relates to a process for the cold production of such preparations.

For centuries, the softly shimmering luster of pearls has held a particular fascination for human beings. It is therefore no wonder that manufacturers of cosmetic preparations, endeavour to give their products an attractive, valuable and rich appearance. The first pearlescence used in cosmetics in the middle ages was a pearlizing paste of natural fish scales. At the beginning of the present century, it was discovered that bismuth oxide chlorides were also capable of producing pearlescence. By contrast, pearlizing waxes, particularly of the glycol monofatty acid ester and difatty acid ester type, are of importance in modern cosmetics, being used mainly for the production of pearlescence in hair shampoos and shower gels. An overview of modern pearlizing formulations was published by A. Ansmann and R. Kawa in Parf. Kosm., 75, 578 (1994).

Various formulations capable of providing surface-active products with the required pearlescence are known from the prior art. For example, German patent applications DE 38 43 572 A1 and DE 41 03 551 A1 (Henkel) describe pearlizing concentrates in the form of free-flowing aqueous dispersions containing 15 to 40% by weight of pearlizing components, 5 to 55% by weight of emulsifiers and 0.1 to 5% by weight or 15 to 40% by weight of polyols. The pearlizing waxes are acylated polyalkylene glycols, monoalkanolamides, linear saturated fatty acids or ketosulfones. European patents EP 0 181 773 B1 and EP 0 285 389 B1 (Procter & Gamble) describe shampoo compositions containing surfactants, non-volatile silicones and pearlizing waxes. European patent application EP 0 205 922 A2 (Henkel) relates to free-flowing pearlizing concentrates containing 5 to 15% by weight of acylated polyglycols, 1 to 6% by weight of fatty acid monoethanolamides and 1 to 5% by weight of nonionic emulsifiers. According to the teaching of European patent EP 0 569 843 B1 (Hoechst), nonionic, free-flowing pearlizing dispersions can also be obtained by preparing mixtures of 5 to 30% by weight of acylated polyglycols and 0.1 to 20% by weight of selected nonionic surfactants. In addition, European patent application EP 0 581 193 A2 (Hoechst) describes free-flowing, preservative-free pearlizing dispersions containing acylated polyglycol ethers, betaines, anionic surfactants and glycerol. Finally, European patent application EP 0 684 302 A1 (Th. Goldschmidt) relates to the use of polyglycerol esters as crystallization aids for the production of pearlizing concentrates.

Commercially available pearlizing waxes have melting points above 80° C. and, accordingly, cannot be incorporated cold into water-based formulations. Because of this, the expert has to use a hot process in which the waxes are melted and allowed to crystallize out slowly in the formulation, the particle fineness of the crystals and hence the brilliance of the pearlescence being a function of the cooling rate. Accordingly, it is immediately clear that hot processes are time-consuming and energy-intensive so that there is a need for a more favorable alterative. In general, therefore, the expert looks to so-called pearlizing concentrates which are more or less concentrated surfactant preparations which already contain the pearlizing waxes in fine-particle, i.e. pearlescent, form and which are stabilized by emulsifiers. Although pearlizing concentrates of the type in question can be further processed cold, the actual problem is not solved in this way and is merely passed onto to the manufacturer of these intermediate products because the concentrates in turn can of course only be obtained by a hot process.

Accordingly, the problem addressed by the present invention was to provide a process for the cold incorporation of pearlizing waxes in surfactant preparations—whether intermediate products, such as pearlizing concentrates for example, or end formulations, such as shampoos for example. At the same time, neither the brilliance of the pearlescence nor the stability of the formulations would be adversely affected by the cold process.

DESCRIPTION OF THE INVENTION

The present invention relates to a process for the cold production of pearlizing surfactant preparations in which aqueous surfactant solutions are initially introduced and mixtures of pearlizing waxes and polyol esters are stirred in at temperatures of 10 to 45° C. and preferably 15 to 25° C.

It has surprisingly been found that even the addition of small quantities of polyol esters reduces the melting point of pearlizing waxes to such an extent that they may readily be incorporated cold (10 to 25° C.) in surfactant-containing formulations. Irrespective of whether the preparations are intermediate products (for example pearlizing concentrates) or end formulations for the consumer (for example shampoos, dishwashing detergents), they have a brilliant pearlescence, are stable in storage and even allow the incorporation of difficult ingredients, such as silicone oils for example. The invention includes the observation that not only pearlescent preparations, but also white, densely opaque preparations can be produced in this way, depending on the type of wax and emulsifier used.

Surfactant-containing Preparations

As already explained, the surfactant-containing preparations may be both intermediate products and pearlizing concentrates or end formulations for the consumer, such as hair shampoos or dishwashing detergents for example. The surfactants present in the preparations may be anionic, nonionic, cationic and/or amphoteric or zwitterionic surfactants which may make up from 1 to 35% by weight, preferably 5 to 15 or 15 to 40% by weight and more preferably 25 to 35% by weight of the preparation, depending on whether it is a concentrate or a dilute solution.

Typical examples of anionic surfactants are soaps, alkyl benzenesulfonates, alkane sulfonates, olefin sulfonates, alkyl ether sulfonates, glycerol ether sulfonates, a-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acyl amino acids such as, for example, acyl lactylates, acyl tartrates, acyl glutamates and acyl aspartates, alkyl oligoglucoside sulfates, protein fatty acid condensates (especially wheat-based vegetable products) and alkyl (ether)phosphates. If the anionic surfactants contain polyglycol ether chains, the polyglycol ether chains may have a conventional homolog distribution, although they preferably have a narrow homolog distribution.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, hydroxy mixed ethers, optionally partially oxidized alk(en)yl oligoglycosides or glucuronic acid derivatives, fatty acid-N-alkyl glucamides, protein hydrolyzates (more particularly wheat-based vegetable products), polyol fatty acid esters, sugar esters, sorbitan esters, polysorbates and amine oxides. If the nonionic surfactants contain polyglycol ether chains, the polyglycol ether chains may have a conventional homolog distribution, although they preferably have a narrow homolog distribution.

Typical examples of cationic surfactants are quatemary ammonium compounds, for example dimethyl distearyl ammonium chloride, and esterquats, more particularly quatemized fatty acid trialkanolamine ester salts.

Typical examples of amphoteric or zwitterionic surfactants are alkylbetaines, alkylamidobetaines, aminopropionates, aminoglycinates, imidazolinium betaines and sulfobetaines.

The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217. The surfactant-containing preparations may contain other typical auxiliaries and additives such as, for example, oil components, superfatting agents, consistency factors, thickeners, polymers, silicone compounds, fats, waxes, stabilizers, biogenic agents, deodorizers, antiperspirants, anti-dandruff agents, film formers, swelling agents, UV protection factors, antioxidants, hydrotropes, preservatives, insect repellents, self-tanning agents, solubilizers, perfume oils, dyes and the like.

Pearlizing Waxes

Suitable pearlizing waxes are, for example, alkylene glycol esters, fatty acid alkanolamides, partial glycerides, esters of polybasic, optionally hydroxysubstituted carboxylic acids, fatty alcohols, fatty acids, fatty ketones, fatty aldehydes, fatty ethers, fatty carbonates, ring opening products of olefin epoxides and mixtures thereof.

The alkylene glycol esters which form component (a1) are normally monoesters and/or diesters of alkylene glycols corresponding to formula (III):

$$R^5CO(OA)_nOR^6 \qquad (III)$$

in which $R^5CO$ is a linear or branched, saturated or unsaturated acyl group containing 6 to 22 carbon atoms, $R^6$ is hydrogen or has the same meaning as $R^5CO$ and A is a linear or branched alkylene group containing 2 to 4 carbon atoms and n is a number of 1 to 5. Typical examples are monoesters and/or diesters of ethylene glycol, propylene glycol, diethylene glycol, dipropylene glycol, triethylene glycol or tetraethylene glycol with fatty acids containing 6 to 22 and preferably 12 to 18 carbon atoms, such as caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Ethylene glycol monostearate and/or distearate is/are particularly preferred.

Fatty acid alkanolamides suitable as pearlizing waxes of group (a2) correspond to formula (IV):

$$R^7CO—NR^8—B—OH \qquad (IV)$$

in which $R^7CO$ is a linear or branched, saturated or unsaturated acyl group containing 6 to 22 carbon atoms, $R^8$ is hydrogen or an optionally hydroxy-substituted alkyl group containing 1 to 4 carbon atoms and B is a linear or branched alkylene group containing 1 to 4 carbon atoms. Typical examples are condensation products of ethanolamine, methyl ethanol-amine, diethanolamine, propanolamine, methyl propanolamine and dipropanolamine and mixtures thereof with caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Stearic acid ethanolamide is particularly preferred.

Partial glycerides which have pearlizing properties and which form component (a3) are monoesters and/or diesters of glycerol with linear, saturated fatty acids, i.e. for example caproic acid, caprylic acid, capric acid, lauric acid, myristic acid, palmitic acid, palmitoleic acid, stearic acid, behenic acid and technical mixtures thereof. They correspond to formula $$\begin{array}{l} CH_2O(CH_2CH_2O)_x—COR^9 \\ | \\ CH—O(CH_2CH_2O)_yR^{10} \\ | \\ CH_2O(CH_2CH_2O)_z—R^{11} \end{array} \qquad (V)$$

in which $R^9CO$ is a linear, saturated acyl group containing 6 to 22 carbon atoms, $R^{10}$ and $R^{11}$ independently of one another represent hydrogen or have the same meaning as $R^9CO$, x, y and z together stand for 0 or for a number of 1 to 30 and X is an alkali or alkaline earth metal, with the proviso that at least one of the two substituents $R^{10}$ and $R_{11}$ is hydrogen. Typical examples are lauric acid monoglyceride, lauric acid diglyceride, coconut fatty acid monoglyceride, coconut fatty acid triglyceride, palmitic acid monoglyceride, palmitic acid triglyceride, stearic acid monoglyceride, stearic acid diglyceride, tallow fatty acid monoglyceride, tallow fatty acid diglyceride, behenic acid monoglyceride, behenic acid diglyceride and technical mixtures thereof which may still contain small quantities of triglyceride from the production process.

Other suitable pearlizing waxes which form component (a4) are esters of polybasic, optionally hydroxysubstituted carboxylic acids with fatty alcohols containing 6 to 22 carbon atoms. Metal salts, more particularly alkali metal slats, of monoesters of dicarboxylic acids or of mono- and/or diesters of tricarboxylic acids are also suitable. In one particular embodiment of the invention, esters of polybasic carboxylic acids, preferably hydroxycarboxylic acids, with partial esters of polyols and metal salts of the corresponding semiesters may also be used as component (a4). The acid component of these esters may be selected, for example, from malonic acid, maleic acid, fumaric acid, adipic acid, sebacic acid, azelaic acid, dodecanedioic acid, phthalic acid, isophthalic acid and, more particularly, succinic acid and also malic acid, citric acid and, more particularly, tartaric acid and mixtures thereof. The fatty alcohols contain 6 to 22, preferably 12 to 18 and more preferably 16 to 18 carbon atoms in the alkyl chain. Typical examples are caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof. The esters may be present as full or partial esters; monoesters and, above all, diesters of carboxylic or hydroxycarboxylic acids preferably being used. Typical examples are succinic acid mono- and dilauryl ester, succinic acid mono- and dicetearyl ester, succinic acid mono- and distearyl ester, tartaric acid mono- and dilauryl ester, tartaric acid mono- and dicocoalkyl ester, tartaric acid mono- and dicetearyl ester, citric acid mono-, di- and trilauryl ester, citric acid mono-, di- and tricocoalkyl ester and citric acid mono-, di- and tricetearyl ester and metal salts thereof, preferably alkali metal salts.

Another group of pearlizing waxes (a5) are fatty alcohols and/or fatty acids corresponding to formula (VI):

$$R^{12}OH \qquad (VI)$$

in which $R^{12}$ is a linear optionally hydroxysubstituted alkyl group and/or acyl group containing 16 to 48 and preferably 18 to 36 carbon atoms. Typical examples of suitable alcohols are cetearyl alcohol, hydroxystearyl alcohol, behenyl alcohol and oxidation products of long-chain paraffins. Examples of acids are stearic acid, hydroxystearic acid and, more particularly behenic acid in a purity of preferably more than 90% by weight. Fatty ketones suitable as component (a6) preferably correspond to formula (VII):

$$R^{13}\text{-O-}R^{1} \qquad (VII)$$

in which $R^{13}$ and $R^{14}$ independently of one another represent alkyl and/or alkenyl groups containing 1 to 22 carbon atoms, with the proviso that they contain a total of at least 24 and preferably 32 to 48 carbon atoms. The ketones may be prepared by known methods, for example by pyrolysis of the corresponding fatty acid magnesium salts. The ketones may be symmetrical or non-symmetrical, although the two substituents $R^{13}$ and $R^{14}$ preferably differ from one another by only one carbon atom and are derived from fatty acids containing 16 to 22 carbon atoms. Stearone is distinguished by particularly advantageous pearlizing properties.

Fatty aldehydes (a7) suitable as pearlizing waxes preferably correspond to formula (VIII):

$$R^{15}COH \qquad (VII)$$

in which $R^{15}CO$ is a linear or branched acyl group containing 24 to 48 and preferably 28 to 38 carbon atoms.

Other suitable pearlizing waxes (a8) are fatty ethers corresponding to formula (IX):

$$R^{16}\text{-O-}R^{17} \qquad (IX)$$

in which $R^{16}$ and $R^{17}$ independently of one another represent alkyl and/or alkenyl groups containing 1 to 22 carbon atoms, with the proviso that they contain a total of at least 24 and preferably 32 to 48 carbon atoms. Fatty ethers of the type mentioned are normally prepared by acidic condensation of the corresponding fatty alcohols. Fatty ethers with particularly advantageous pearlizing properties are obtained by condensation of fatty alcohols containing 16 to 22 carbon atoms such as, for example, cetyl alcohol, cetearyl alcohol, stearyl alcohol, isostearyl alcohol, oleyl alcohol, behenyl alcohol and/or erucyl alcohol.

Other suitable pearlizing waxes (a9) are fatty carbonates corresponding to formula (X):

$$R^{18}OCO\text{-}OR^{19} \qquad (X)$$

in which $R^{18}$ and $R^{19}$ independently of one another are alkyl and/or alkenyl groups containing 1 to 22 carbon atoms, with the proviso that they contain a total of at least 24 and preferably 32 to 48 carbon atoms. The substances are obtained by transesterifying dimethyl or diethyl carbonate, for example, with the corresponding fatty alcohols by methods known per se. Accordingly, the fatty carbonates may be symmetrical or non-symmetrical. However, carbonates in which $R^{18}$ and $R^{19}$ are the same and represent alkyl groups containing 16 to 22 carbon atoms are preferably used. Transesterification products of dimethyl or diethyl carbonate with cetyl alcohol, cetearyl alcohol, stearyl alcohol, isostearyl alcohol, oleyl alcohol, behenyl alcohol and/or erucyl alcohol in the form of their monoesters and diesters and technical mixtures thereof are particularly preferred.

Finally, the ring-opening products which form group (a10) are known substances which are normally obtained by acid-catalyzed reaction of terminal or internal olefin epoxides with aliphatic alcohols. The reaction products preferably correspond to formula (XI):

(XI)

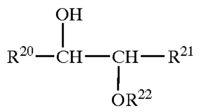

in which $R^{20}$ and $R^{21}$ represent hydrogen or an alkyl group containing 10 to 20 carbon atoms, with the proviso that the sum total of carbon atoms of $R^{20}$ and $R^{21}$ is between 10 and 20 and $R^{22}$ is an alkyl and/or alkenyl group containing 12 to 22 and/or the residue of a polyol containing 2 to 15 carbon atoms and 2 to 10 hydroxyl groups. Typical examples are ring-opening products of x-dodecene epoxide, x-hexadecene epoxide, a-octadecene epoxide, a-eicosene epoxide, a-docosene epoxide, i-dodecene epoxide, i-hexadecene epoxide, i-octadecene epoxide, i-eicosene epoxide and/or i-docosene epoxide with lauryl alcohol, cocofatty alcohol, myristyl alcohol, cetyl alcohol, cetearyl alcohol, stearyl alcohol, isostearyl alcohol, oleyl alcohol, elaidyl alcohol, petroselinyl alcohol, linolyl alcohol, linolenyl alcohol, behenyl alcohol and/or erucyl alcohol. Ring opening products of hexa- and/or octadecene epoxides with fatty alcohols containing 16 to 18 carbon atoms are preferably used. If polyols are used instead of the fatty alcohols for the ring opening reaction, they are selected for example from the following substances: glycerol; alkylene glycols such as, for example, ethylene glycol, diethylene glycol, propylene glycol, butylene glycol, hexylene glycol and polyethylene glycols with an average molecular weight of 100 to 1,000 dalton; technical oligoglycerol mixtures with a degree of self-condensation of 1.5 to 10 such as, for example, technical diglycerol mixtures with a diglycerol content of 40 to 50% by weight; methylol compounds such as, in particular, trimethylol ethane, trimethylol propane, trimethylol butane, pentaerythritol and dipentaerythritol; lower alkyl glucosides, more particularly those containing 1 to 8 carbon atoms in the alkyl chain such as, for example, methyl and butyl glucoside; sugar alcohols containing 5 to 12 carbon atoms such as, for example, sorbitol or mannitol, sugars containing 5 to 12 carbon atoms such as, for example, glucose or sucrose; amino sugars such as, for example, glucamine. If G. pearlizing concentrates are to be produced by the process according to the invention, the pearlizing waxes normally make up from 5 to 45%, preferably from 10 to 45 and more preferably from 25 to 35% by weight of the preparations. In the case of end formulations, the pearlescence content is of course far lower and is typically from 0.5 to 3% by weight and preferably from 1 to 2% by weight.

Polyol Esters

Polyol esters which are used in accordance with the invention to lower the melting point of the pearlizing waxes may be selected from the following groups of compounds:

- partial esters of glycerol and/or sorbitan with unsaturated, linear or saturated, branched fatty acids containing 12 to 22 carbon atoms and/or hydroxycarboxylic acids containing 3 to 18 carbon atoms and adducts thereof with 1 to 30 mol of ethylene oxide;
- partial esters of polyglycerol (average degree of self-condensation 2 to 8), polyethylene glycol (molecular weight 400 to 5000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and adducts thereof with 1 to 30 mol ethylene oxide;
- mixed esters of pentaerythritol, fatty acids, citric acid and fatty alcohol according to DE 11 65 574 PS and/or mixed esters of fatty acids containing 6 to 22 carbon atoms, methyl glucose and polyols, preferably glycerol or polyglycerol.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide with the partial glycerides mentioned are also suitable.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl4 Isostearate (Isolan® GI 34), Polyglyceryl-3 Oleate, Diisostearoyl Polyglyceryl-3 Diisostearate (Isolan® PDI), Poly-glyceryl-3 Methylglucose Distearate (Tego Care® 450), Polyglyceryl-3 Beeswax (Cera Bellina®), Polyglyceryl4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof.

Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

If pearlizing concentrates are to be produced by the process according to the invention, the polyolesters typically make up from 0.5 to 15% by weight, preferably from 1 to 10% by weight and more preferably from 5 to 8% by weight of the preparations. In the case of end formulations, the polyol ester content is of course far lower and is typically from 0.1 to 1% by weight and preferably about 0.5% by weight. As a rule, the polyol ester content, based on the quantity of pearlizing wax, is typically from 1 to 15% by weight and preferably from 5 to 10% by weight.

Emulsifiers

As already mentioned, the surfactant-containing preparations may basically contain any type of surfactant, the choice of surfactant being determined solely by the desired performance profile for the particular end use. In a preferred embodiment of the invention, however, the surface-containing preparations are pearlizing concentrates, i.e. intermediate products. In this case, the choice of the surfactant component is more critical because the requirement profile consists primarily in permanently stabilizing large amounts of the pearlizing wax and at the same time keeping the viscosity of the preparations so low that they can still be readily pumped and dosed. This purpose may be served, for example, by nonionic surfactants from at least one of the following groups:

- products of the addition of 2 to 30 mol ethylene oxide and/or 0 to 5 mol propylene oxide onto linear fatty alcohols containing 8 to 22 carbon atoms, onto fatty acids containing 12 to 22 carbon atoms, onto alkylphenols containing 8 to 15 carbon atoms in the alkyl group and onto alkylamines containing 8 to 22 carbon atoms in the alkyl group;
- alkyl mono- and oligoglycosides containing 8 to 22 carbon atoms in the alkyl group and ethoxylated analogs thereof;
- products of the additon of 1 to 15 mol ethylene oxide onto castor oil and/or hydrogenated castor oil;
- products of the addition of 15 to 60 mol ethylene oxide onto castor oil and/or hydrogenated castor oil;
- mono-, di- and trialkyl phosphates and mono-, di- and/or tri-PEG-alkyl phosphates and salts thereof;
- wool wax alcohols;
- polysiloxane/polyalkyl polyether copolymers and corresponding derivatives;
- polyalkylene glycols and
- glycerol carbonate.

The addition products of ethylene oxide and/or propylene oxide onto fatty alcohols, fatty acids, alkylphenols or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as refatting agents for cosmetic preparations from DE 20 24 051 PS. $C_{8/18}$ alkyl mono- and oligoglycosides, their production and their use are known from the prior art. They are produced in particular by reacting glucose or oligosaccharides with primary $C_{8-18}$ alcohols. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocoamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH—or —$SO_3$H—group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{2/18}$ acyl sarcosine.

Finally, cationic surfactants are also suitable emulsifiers, those of the esterquat type, preferably methyl-quaternized difatty acid triethanolamine ester salts, being particularly preferred.

Polyols

If highly concentrated pearlizing concentrates are to be produced, it can be of advantage to use polyols to lower the viscosity. Suitable polyols preferably contain 2 to 15 carbon atoms and at least two hydroxyl groups. The polyols may contain other functional groups, more especially amino groups, or may be modified with nitrogen. Typical examples are

- glycerol;
- alkylene glycols such as, for example, ethylene glycol, diethylene glycol, propylene glycol, butylene glycol, hexylene glycol and polyethylene glycols with an average molecular weight of 100 to 1000 dalton;
- technical oligoglycerol mixtures with a degree of self-condensation of 1.5 to 10 such as, for example, technical diglycerol mixtures with a diglycerol content of 40 to 50% by weight;
- methylol compounds such as, in particular, trimethylol ethane, trimethylol propane, trimethylol butane, pentaerythritol and dipentaerythritol;
- lower alkyl glucosides, particularly those containing 1 to 8 carbon atoms in the alkyl group, for example methyl and butyl glucoside;
- sugar alcohols containing 5 to 12 carbon atoms, for example sorbitol or mannitol;
- sugars containing 5 to 12 carbon atoms, for example glucose or sucrose;
- amino sugars, for example glucamine;
- dialcoholamines, such as diethanolamine or 2-aminopropane-1,3-diol.

The polyols are used in quantities of typically 0.1 to 15 and preferably 0.5 to 5% by weight, based on the surfactant-containing preparations. If larger quantities of polyol, preferably glycerol or ethylene glycol, are used, the concentrates are simultaneously stabilized against microbial infestation.

Production Process

The surfactant-containing preparations are normally produced by initially introducing an aqueous surfactant or emulsifier mixture, optionally together with other auxiliaries and additives, at 10 to 25° C., introducing the mixture of pearlizing wax and polyol ester at that temperature and homogenizing the whole followed by crystallization. In an alternative method of production, a concentrated aqueous (anionic) surfactant paste may be initially introduced, the mixture of pearlizing wax and polyolester stirred in cold and the mixture subsequently diluted with more water to the required concentration or the mixing step may be carried out in the presence of polymeric hydrophilic thickeners such as, for example, hydroxypropyl celluloses, xanthan gum or polymers of the Carbomer type. Finally, the mixture of pearlizing wax and polyol ester may also be dissolved or dispersed in part of the aqueous surfactant solution and then mixed with the main quantity of the preparation.

Examples

The melting-point-lowering effect of adding polyol esters to commercially available pearlizing waxes is illustrated in Table 1. The pure waxes and mixtures of 90% by weight wax and 10% by weight polyol ester were compared. Shampoos with the following composition were then prepared: 12 g cocofatty alcohol+2EO sulfate sodium salt, 1.5 g dimethyl polysiloxane, 3 g cocoalkyl glucoside and 1.5 g of an esterquat (water to 100% by weight). The preparations were (a) heated to 90° C. and, after addition of 1 g of pearlizing waxes C1 to C4, were cooled to ambient temperature over 1 hour or (b) mixtures 1 to 4 were added in quantities of 1 g at 20° C. The particle fineness of the pearlescent crystals in the hair shampoos was visually evaluated under a microscope on a scale of 1=very fine crystals to 5=coarse crystals. Pearlescence was also evaluated on a scale of 1=sparkling to 5=dull. The results are also set out in Table 1.

TABLE 1

Melting point reduction of pearlizing waxes and performance in shampoos (quantities as % by weight)

| Composition/performance | C1 | C2 | C3 | C4 | 1 | 2 | 2 | 4 |
|---|---|---|---|---|---|---|---|---|
| Ethyleneglycol Distearate | 100 | — | — | — | 90 | — | — | — |
| Glyceryl Stearate | — | 100 | — | — | — | 90 | | |
| Distearyl Ether | — | — | 100 | — | — | — | 90 | |
| Distearyl Malate | — | — | — | 100 | — | — | — | 90 |
| Sorbitan Oleate | — | — | — | — | 10 | — | — | — |
| PEG-3 Trimethylolpropane Distearate | — | — | — | — | — | 10 | — | — |
| Polyglyceryl-2-Dipolyhydroxystearate | — | — | — | — | — | — | 10 | — |
| Polyglycerin-3-Diisostearate | — | — | — | — | — | — | — | 10 |
| Melting point [° C.] | 60 | 58 | 60 | 60 | 45 | 45 | 44 | 44 |
| Pearlescence in the formulation | | | | | | | | |
| Brilliance | 1.5 | 1.5 | 1.5 | 1.5 | 1.5 | 1.5 | 1.5 | 1.5 |
| Particle fineness | 1.0 | 1.0 | 1.0 | 1.0 | 1.0 | 1.0 | 1.0 | 1.0 |

What is claimed is:

1. A process for the cold production of a pearlizing surfactant composition comprising the steps of: (1) providing an aqueous surfactant solution; (2) contacting the aqueous surfactant solution with a composition comprised of a pearlizing wax and a polyol ester at a temperature of from about 10° C. to about 45° C.

2. The process of claim 1 wherein the surfactant is selected from the group consisting of an anionic surfactant, a nonionic surfactant, a cationic surfactant, an amphoteric surfactant, and a zwitterionic surfactant.

3. The process of claim 1 wherein the concentration of the surfactant in the aqueous surfactant solution is from about 1% to about 35% by weight.

4. The process of claim 3 wherein the concentration of the surfactant is from about 5% to about 15% by weight.

5. The process of claim 3 wherein the concentration of the surfactant is from about 25% to about 35% by weight.

6. The process of claim 1 wherein the pearlizing wax is selected from the group consisting of an alkylene glycol ether, a fatty acid alkanolamide, a partial glyceride, an ester of a polybasic carboxylic acid, an ester of a hydroxy-susbstituted polybasic carboxylic acid, a fatty alcohol, a fatty acid, a fatty ketone, a fatty aldehyde, a fatty ether, a fatty carbonate, and a ring opening product of an olefin epoxide.

7. The process of claim 1 wherein the polyol ester is selected from the group consisting of a partial ester of glycerol or sorbitan wherein the acid portion of the ester is a saturated or unsaturated, linear or branched fatty acid having from about 12 to about 22 carbon atoms or a hydroxy-substituted carboxylic acid having from about 3 to about 18 carbon atoms and adducts thereof having from 1 to about 30 moles of ethylene oxide; a partial ester of polyglycerol, polyethylene glycol, trimethylol propane, pentaerythritol, an alkyl polyglucoside wherein the acid portion of the ester is a saturated or unsaturated, linear or branched fatty acid having from about 12 to about 22 carbon atoms or a hydroxy-substituted carboxylic acid having from about 3 to about 18 carbon atoms and adducts thereof having from 1 to about 30 moles of ethylene oxide; mixed esters of pentaerythritol, fatty alcohols and fatty acids and citric acid; mixed esters of fatty acids having from about 6 to about 22 carbon atoms; a mixture of methyl glucose and a polyol.

8. The process of claim 1 wherein the polyolester is present in an amount of from about 0.1% to about 15% by weight.

9. The process of claim 1 wherein when the surfactant concentration is from about 15% to about 40% by weight, the surfactant solution is further comprised of adducts of from about 2 to about 30 moles of ethylene glycol, from 0 to about 5 moles of propylene glycol or a combination thereof with linear fatty alcohols having from about 8 to about 22 carbon atoms or fatty acids having from about 12 to about 22 carbon atoms or alkyl phenols having from about 8 to about 15 carbon atoms in the alkyl group or alkyl amines having from about 8 to about 22 carbon atoms in the alkyl group; alkyl mono- and oligoglycosides having from about 8 to about 22 carbon atoms in the alkyl group; addition products of castor oil or hydrogenated castor oil and from about 1 to about 15 moles of ethylene oxide or from about 15 to about 60 moles ethylene oxide; a di- or tri-PEG alkyl phosphate and salts thereof; a wool wax alcohol; a copolymer of polysiloxane and a polyalkyl ether; a polyalkylene glycol; a glycerol carbonate; a cocamidopropyl betaine and an ester quat.

* * * * *